Dec. 13, 1960 O. O. DUNHAM Plant Pat. 2,007
CHRYSANTHEMUM PLANT
Filed July 27, 1959
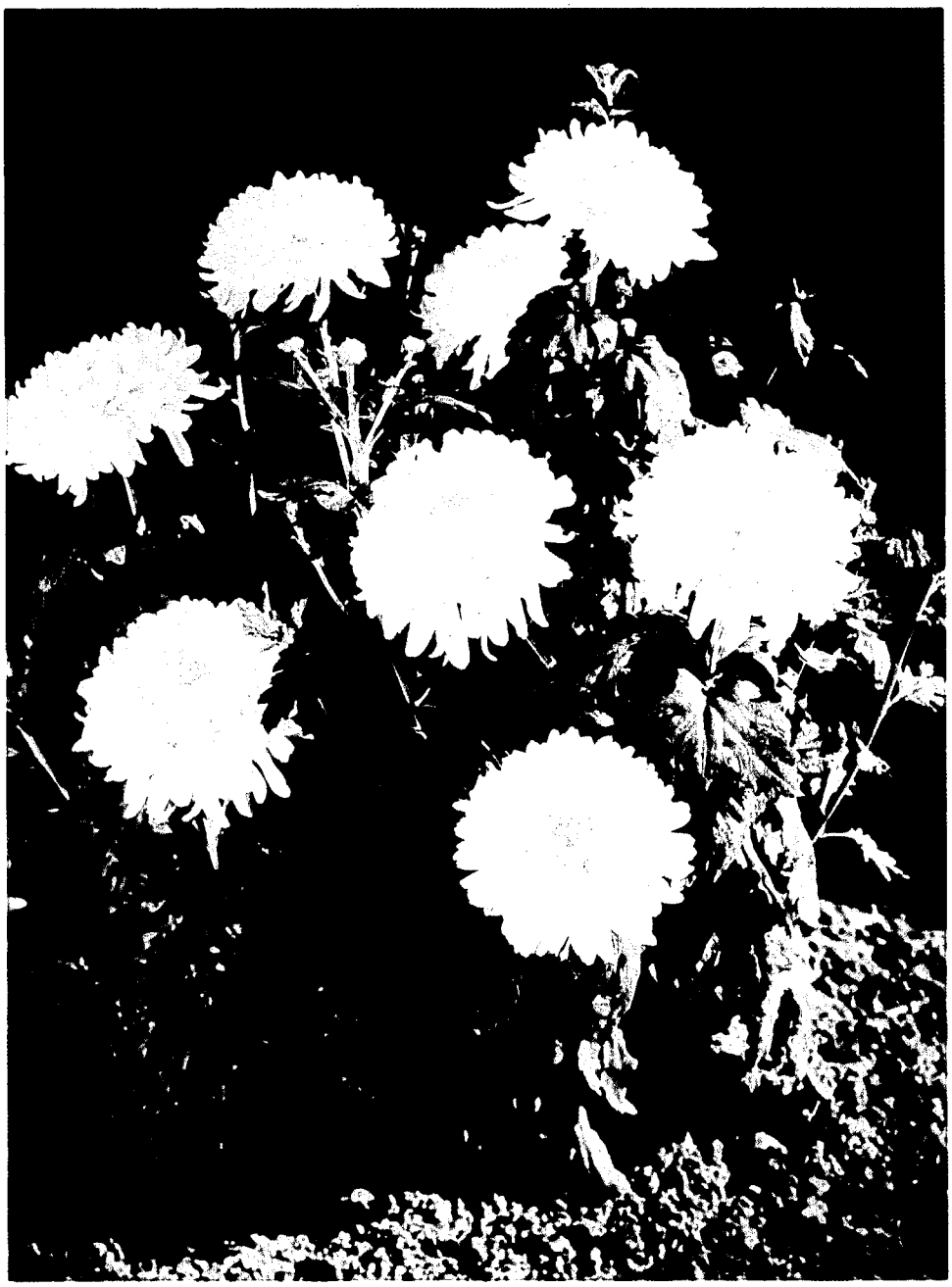
Inventor
O. O. Dunham
by
Robbs & Robbs
Attorneys United States Patent Office Plant Pat. 2,007
Patented Dec. 13, 1960

2,007

CHRYSANTHEMUM PLANT

Orville O. Dunham, Niles, Mich., assignor to George J. Ball, Inc., West Chicago, Ill., a corporation of Illinois Filed July 27, 1959, Ser. No. 829,950

1 Claim. (Cl. 47—60)

My present invention comprises a new and distinct variety of chrysanthemum plant, which is the result of crossing the variety "Freedom" (unpatented) a variety of my own introduction, and the unpatented variety "Ermine."

The object of my invention has been to produce a new variety of chrysanthemum of the indicum type in which the plant habit is better than the parents and more compact with better flower form than such parents.

The development of my present new variety is the result of a careful program of selection and cross breeding in which generally speaking so-called American garden chrysanthemums have been crossed with the so-called English early chrysanthemums, in an endeavor to retain the best characteristics of each with a large number of different colors and an improvement in habits of growth, generally speaking.

The result of the specific hybridization previously mentioned has been to produce my present new and distinct variety of chrysanthemum plant characterized by the lighter than brilliant yellow, more closed center, white general tonality, and the large size and hardiness of its blooms, the very double arrangement of its petals, the earlier, continuous and long blooming period, and its better habit and larger and more abundant foliage. A very important advantage of the hybrids which have been generally referred to derived as a result of my program of hybridization, is to improve upon the habit of the English early chrysanthemums so as to produce varieties which are much more compact. However it is also desirable to take advantage of the continuous flowering feature of the English early chrysanthemum in contrast to the flowering of the American garden chrysanthemums which takes place over a very short period of time relatively speaking under ordinary conditions.

More specifically, the blooms of my new variety are of a pure white over-all general tonality with a lighter than brilliant yellow center, the center being very closed. (Nickerson Color Fan—Munsell Color Company.)

While my new variety bears a resemblance to both its parents, in the white over-all tonality, it has a much better plant habit than either and differs from other known varieties in many respects.

The comparison of the color of the blooms of my new variety with the color of the blooms of the variety "Freedom" calls attention to the fact that my new variety has the lighter than brilliant yellow closed center. In contrasting the plant of my new variety with the parent "Ermine" it is noted that the new variety is much more compact than "Ermine" which is quite tall. In addition the flower of "Ermine" has a tendency to show an open center whereas the flower of my new variety is quite closed.

Under the conditions of culture previously mentioned which took place in the region of Niles, Michigan, the plant habits and foliage of my new variety have appeared to be better than the parents, with the new variety being more compact but much bushier with a somewhat spreading tendency.

The new variety when grown in the region of Niles, Michigan, blooms from mid-September and profusely and continuously until the killing frost.

The foliage of my new variety has been found to be more abundant and somewhat smoother texture and rather large generally.

My new variety has been asexually reproduced by cuttings, in the vicinity of Niles, Michigan.

My new variety has been found to retain its distinctive characteristics through successive asexual reproductions.

The accompanying drawing, forming a part hereof, shows a typical plant of my new variety of chrysanthemum.

The following is a detailed description of my new variety of chrysanthemum plant, the color references being to the Nickerson Color Fan published by Munsell Color Company:

Parentage: Seedling.
- *Seed parent.*—"Ermine' (unpatented).
- *Pollen parent.*—"Freedom" (unpatented).

Classification: Botanic—*Chrysanthemum indicum.*

*Flower*

Blooming habit: Blooms profusely, early in the season about mid-September until a killing frost, continuously, the observations of this flower having been made in October.

Bud:
- *Size.*—Large.
- *Form.*—Short with flat top. Not affected by wet or hot weather. Sepals of no consequence.
- *Color.*—When petals begin to unfurl—white shading to cream white. When half blown: inside of petals—white; reverse of petals—white.
- *Peduncle.*—Very long.
- *Aspect.*—Rough.
- *Color.*—Medium green.
- *Strength.*—Stiff; erect.
- *Opening.*—Bud opens well. Somewhat affected by adverse conditions.

Bloom:
- *Size.*—Large.
- *Average size when fully expanded.*—5¼ inches (disbudded).
- *Borne.*—In clusters; irregular.
- *Stems.*—Long; strong.
- *Form.*—Flat. Permanence—retains its form to the end.
- *Petalage.*—Very double. Number of petals under normal conditions—innumerable.
- *Color.*—Center of flower—lighter than 2.5Y 9/9—Munsell Hue 2.5Y. Outer petals—white. Base of petals—lighter than 2.5Y 9/9—Munsell Hue 2.5Y. Inside of petals — white. Reverse of petals—white. General tonality—white.
- *Discolorations.*—First week—retains same color. Second week—retains much the same color. Third week—retains much the same color.

Petals:
- *Texture.*—Thin. Bleaches in hot weather. Susceptible to fungus infection in wet weather.
- *Appearance.*—Inside—velvety. Outside—satiny.
- *Form.*—pointed.
- *Arrangement.*—Imbricated.
- *Persistence.*—Hang on and dry.
- *Lastingness.*—On the plant—very long. As cut flower—long.

Genital organs:
- *Stamens, anthers.*—Small; few. Color—yellow. Arrangement—regular around styles.

*Stamens, filaments.*—Short. Color—white.
*Styles.*—Columnar. Length—short.
*Stigmas.*—White in color.
*Ovaries.*—All enclosed in calyx.
Fruit: Variety is fertile with own pollen.
*Form.*—Oblong shaped.
*Aspect.*—Rough.
*Color at maturity.*—Brownish grey.

*Plant*

Form: Bush.
Growth: Vigorous; dwarf; branching; compact.
Foliage:
*Size.*—Large.
*Quantity.*—Abundant.
*Color.*—New foliage: upper side—normal green; under side—light green. Old foliage: upper side—dark green; under side—dark green.
*Shape.*—Three lobed.

*Texture.*—Smooth; flat—upper side. Under side—velvety. Ribs and veins—ordinary.
*Edge.*—Smooth.
*Leaf stem.*—Green in color. Smooth under side.
*Stipules.*—Short.
*Disease resistant.*—Susceptible to mildew under certain conditions.

I claim:

A new and distinct variety of chrysanthemum plant substantially as herein disclosed, characterized as to novelty by the lighter than brilliant yellow, more closed center, white general tonality, and the large size and hardiness of its blooms, the very double arrangement of its petals, the earlier, continuous, and long blooming period, its better habit, and larger and more abundant foliage.

No references cited.